(12) United States Patent
Flaherty et al.

(10) Patent No.: US 6,768,425 B2
(45) Date of Patent: Jul. 27, 2004

(54) MEDICAL APPARATUS REMOTE CONTROL AND METHOD

(75) Inventors: J. Christopher Flaherty, Topsfield, MA (US); John T. Garibotto, Charlestown, MA (US)

(73) Assignee: Insulet Corporation, Beverly, MA (US)

(*) Notice: Subject to any disclaimer, the term of this patent is extended or adjusted under 35 U.S.C. 154(b) by 414 days.

(21) Appl. No.: 10/032,167

(22) Filed: Dec. 21, 2001

(65) Prior Publication Data

US 2002/0126036 A1 Sep. 12, 2002

Related U.S. Application Data

(60) Provisional application No. 60/257,756, filed on Dec. 21, 2000.

(51) Int. Cl.[7] .................................................. H04Q 9/00
(52) U.S. Cl. .................. 340/870.07; 128/920; 604/132; 604/890.1; 604/892.1
(58) Field of Search ..................... 340/870.07; 600/300; 128/903, 820; 604/65–67, 95.01, 132, 890.1, 892.1

(56) References Cited

U.S. PATENT DOCUMENTS

| 3,631,847 A | 1/1972 | Hobbs |
| 3,812,843 A | 5/1974 | Wootten et al. |
| 4,067,000 A | 1/1978 | Carlson |

(List continued on next page.)

FOREIGN PATENT DOCUMENTS

| DE | 4200595 | 7/1993 |
| DE | 19920896 | 9/2000 |
| EP | 0342947 | 5/1989 |
| EP | 0763369 | 3/1997 |
| EP | 0867196 | 3/1998 |
| EP | 0937475 | 8/1999 |
| WO | WO81/01658 | 6/1981 |
| WO | WO86/06796 | 11/1986 |
| WO | WO98/01071 | 1/1998 |
| WO | WO99/10040 | 3/1999 |
| WO | WO00/19887 | 9/1999 |
| WO | WO99/62576 | 9/1999 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO00/61215 | 10/2000 |
| WO | WO01/52727 | 1/2001 |
| WO | WO01/76684 | 10/2001 |
| WO | WO 02/20073 | 3/2002 |
| WO | WO02/26282 | 4/2002 |

OTHER PUBLICATIONS

US 5,954,699, 9/1999, Jost et al. (withdrawn)
Web–Site Brochure dated Jan. 4, 2000. MiniMed 508. "Doing its job. Naturally." www.minimed.com/tiles/mm_113.htm.

*Primary Examiner*—Timothy Edwards, Jr.
(74) *Attorney, Agent, or Firm*—McDermott Will & Emery LLP

(57) ABSTRACT

A system for providing medical treatment to a patient, including a medical treatment apparatus and a remote control device. The medical treatment apparatus has a local processor, and a local communication element connected to the local processor, while the remote control device includes a remote processor, user interface components connected to the remote processor, and a remote communication element connected to the remote processor and adapted to communicate with the local communication element of the medical treatment apparatus in a wireless manner such that information can be transferred between the local processor and the remote processor. The remote control device also includes at least two separate power supplies connected to the remote processor.

67 Claims, 7 Drawing Sheets

U.S. PATENT DOCUMENTS

| | | |
|---|---|---|
| 4,108,177 A | 8/1978 | Pistor |
| 4,151,845 A | 5/1979 | Clemens |
| 4,193,397 A | 3/1980 | Tucker et al. |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| D303,013 S | 8/1989 | Konopka |
| 4,855,746 A | 8/1989 | Stacy |
| 4,871,351 A | 10/1989 | Feingold |
| 4,882,600 A | 11/1989 | Van de Moere |
| 4,886,499 A | 12/1989 | Cirelli et al. |
| 4,898,579 A | 2/1990 | Groshong et al. |
| D306,691 S | 3/1990 | Arai |
| 4,944,659 A | 7/1990 | Labbe et al. |
| D311,735 S | 10/1990 | Aran et al. |
| 4,969,874 A | 11/1990 | Michel et al. |
| 4,973,998 A | 11/1990 | Gates |
| D315,727 S | 3/1991 | Arai et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,178,609 A | 1/1993 | Ishikawa |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Böcker et al. |
| 5,514,096 A | 5/1996 | Hiejima |
| 5,533,389 A | 7/1996 | Kamen et al. |
| 5,545,152 A | 8/1996 | Funderburk et al. |
| 5,551,953 A * | 9/1996 | Lattin et al. .................. 604/20 |
| 5,575,770 A | 11/1996 | Melsky et al. |
| 5,576,781 A | 11/1996 | Deleeuw |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| D405,524 S | 2/1999 | Falk et al. |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,171,264 B1 * | 1/2001 | Bader .................. 600/595 |
| 6,174,300 B1 | 1/2001 | Kriesel et al. |
| 6,190,359 B1 | 2/2001 | Heruth |
| 6,206,850 B1 | 3/2001 | O'Neil |
| 6,375,638 B2 | 4/2002 | Nason et al. |
| 6,520,936 B1 | 2/2003 | Mann |
| 6,527,744 B1 | 3/2003 | Kriesel et al. |
| 6,554,798 B1 * | 4/2003 | Mann et al. ................. 604/131 |

| | | | |
|---|---|---|---|
| 6,558,320 B1 * | 5/2003 | Causey et al. | 600/300 |
| 6,645,142 B2 * | 11/2003 | Braig et al. | 600/300 |

OTHER PUBLICATIONS

Web–Site Brochure dated Dec. 20, 1999. Applied Medical Technology. "508 Pump Information". www.applied-medical.co.uk/508.htm.

Web–Site Brochure dated Jan. 4, 2000. "The Glucose Sensor". www.animascorp.com/sensor_f.html.

Web–Site Brochure dated Dec. 20, 1999. "The Animas R–1000 Insulin Pump". www.animascorp.com/pump_f_s.html.

Web–Site Brochure dated Dec. 20, 1999. "The Animas R–1000 Insulin Pump". www.animascorp.com/pump_f_f.html.

Web–Site Brochure dated Jan. 4, 2000. SOOIL–Homepage. "Portable Insulin Pump". www.sooil.com/intro2.htm.

Web–Site Brochure dated Jan. 4, 2000. SOOIL–Homepage. "Portable Insulin Pump". www.sooil.com/product2.htm.

Web–Site Brochure dated Jan. 4, 2000. SOOIL–Homepage. "Portable Insulin Pump". www.sooil.com/product3.htm.

Web–Site Brochure dated Jan. 4, 2000. SOOIL–Homepage. "Portable Insulin Pump". www.sooil.com/product4.htm.

Copy of International Search Report.

* cited by examiner

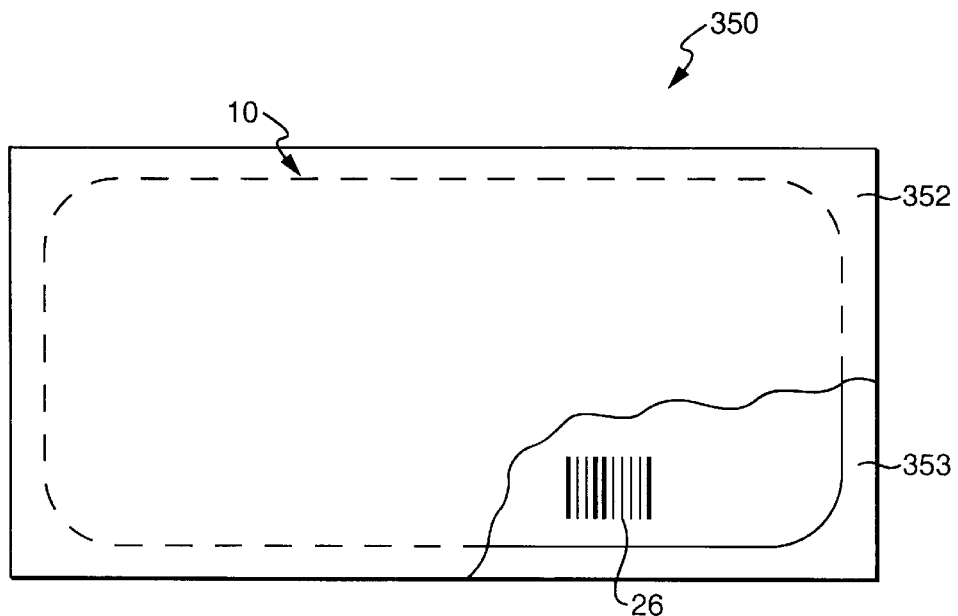
FIG. 6
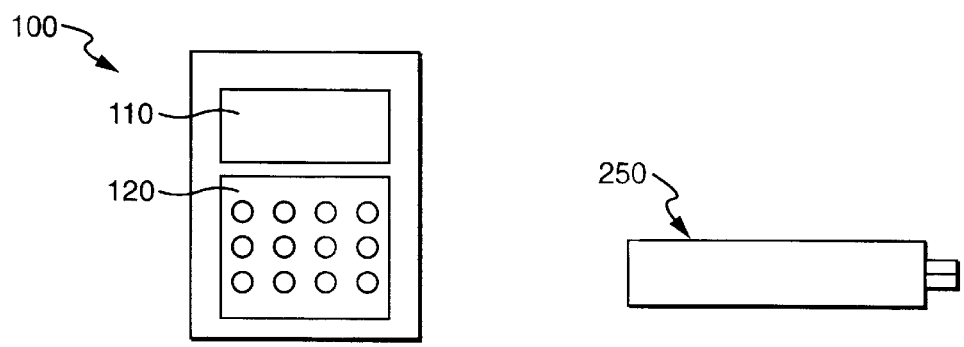
FIG. 6A
FIG. 6B

MEDICAL APPARATUS REMOTE CONTROL AND METHOD

CROSS-REFERENCE TO RELATED APPLICATIONS

The present application claims priority to provisional U.S. patent application Ser. No. 60/257,756, filed on Dec. 21, 2000, which is assigned to the assignee of the present application and incorporated herein by reference. The present application is related to U.S. patent application Ser. No. 09/943,992, filed on Aug. 31, 2001, which is assigned to the assignee of the present application and incorporated herein by reference.

FIELD OF THE INVENTION

The present invention relates generally to handheld devices that perform multiple functions, and more particularly to a handheld device for remotely controlling one or more medical apparatuses in addition to performing other functions for a user.

BACKGROUND OF THE INVENTION

Today, there are various handheld electronic devices that are routinely carried by a large portion of the population on a daily basis. Examples of these devices include cellular telephones such as those offered by Nokia or Motorola, personal digital assistants (PDA's) such as those offered by Palm, Inc., handheld electronic games such as the Lunker Bass Fishing game by Radica, garage door openers, and various other handheld electronic devices that perform specific functions for a user. In recent years, technological advances have allowed significant enhancements in such handheld electronic devices including reduced size and weight, longer battery life, simplified user interfaces, and other additional new features and improvements. For example, the addition of a touch screen panel, such as that incorporated into the Palm Pilot personal digital assistant, allows simple menu driven access to personal calendars, address books, to-do lists and email.

Other handheld electronic devices include remote control devices such as those commonly supplied with televisions, video cassette recorders (VCR's), and DVD players. Using wireless communication, such as radio frequency, infrared or ultrasound, these remote control devices allow a user to control separate electronic equipment without having to be in proximity to or otherwise have access to the controls of the separate electronic equipment.

Various medical apparatus can be controlled with a remote control device as well. Examples of these devices include x-ray machines, operating tables, diagnostic monitors, and drug infusion devices. The medical apparatus remote control devices provide similar advantages to television or VCR remote control devices, obviating the need for a user to be proximal to or have access to the controls of the medical apparatus.

As handheld electronic devices and remote control devices have become widespread in their use, it has become desirable to combine multiple products or functions into single devices. Such devices having multiple functions do exist, but usually the particular grouping of functions are related, such as the "universal remotes" available for televisions, VCRs, and other home audiovisual equipment remote control devices. In U.S. Pat. No. 4,855,746, for example, Stacy shows a multi-device remote control with an array of keys that are exposed in pre-selected groups by moving a slidable cover. A position of the slidable cover determines which device the remote control device will control and the type of coded control signals that the remote control device will transmit. Other examples of devices having multiple functions include some recent cellular telephones, which have been manufactured with personal computer functions, electronic address and calendar functions, and built-in internet access.

User controlled ambulatory infusion devices can be an ideal use for a remote control. Ambulatory infusion pumps have been developed for delivering liquid medicaments to a patient. These infusion devices have the ability to offer sophisticated fluid delivery profiles accomplishing bolus requirements, continuous infusion and variable flow rate delivery, which can result in better efficacy of the drug and therapy and less toxicity to a patient's system. An example of a use of an ambulatory infusion pump is for continuous subcutaneous infusion of insulin to diabetic patients. Many diabetics require insulin intake to treat their disease, and continuous subcutaneous infusion of insulin from an infusion pump has been shown in numerous studies to greatly improve the immediate and long term health conditions of those patients. These pumps can deliver insulin on a continuous basal basis as well as a bolus basis as shown, for example, in U.S. Pat. No. 4,498,843 to Schneider et al.

User controlled ambulatory infusion devices are an ideal use for a remote control since the infusion devices may be located out of reach of a patient, or may be discreetly located beneath clothing or in a carrying pouch. Since the diabetic patient utilizing an ambulatory infusion pump may wish to place the device beneath their clothing, for added comfort and or for privacy, a remote control device is appropriate to adjust various parameters associated with the infusion pump, or simply to review pump status or other pump information. These patients may also carry a glucose measuring device such as a glucometer as well as a cellular phone, pager, PDA or other handheld electronic device not directly associates with the treatment of their health condition. Ambulating with multiple handheld devices such as these can be fraught with issues not the least of which is contusion, and the increased probability of losing one of the devices.

Certain ambulatory infusion devices may be designed to be of limited life or even disposable. For example, U.S. patent application Ser. No. 09/943,992, filed on Aug. 31, 2001, which is assigned to the assignee of the present application and incorporated herein by reference discloses a remotely controlled, disposable infusion pump. In such cases, it would be desirable to provided a non-disposable remote control device that can be used to control successive disposable pumps.

If a handheld electronic device is to be used for controlling a medical apparatus, such as an infusion pump, certain prioritization of performance may be desired. One such prioritization, for example, relates to power consumption. As most of today's handheld devices are powered by a replaceable or rechargeable battery, it may be desirable to regulate power consumption and low battery conditions in a specialized manner. In U.S. Pat. No. 4,514,732, for example, Hayes shows power conservation methods for particular commands of a remote control for electronic audiovisual equipment. When a user continually presses a key on the remote control, such as to decrease volume, the remote control is programmed to send a single command signal to the equipment to start decreasing volume when the user initially presses the button, and to send a single command signal to stop decreasing volume when the button is released. Hayes' method avoids sending a continuous stream of signals to dictate the volume decrease in the equipment, thus reducing the power consumption of the remote control.

Some electronic handheld devices and remote controls include low battery warnings via an audible alert, screen message or other visual low battery indicator. Often, these devices are used until the batteries contain insufficient energy to power the device at which time the batteries are replaced or recharged. However, for controlling medical treatment apparatus, such down time due to lack of new batteries could be very undesirable.

Accordingly, there continues to be a need for remote control devices which can be used with medical treatment apparatus, such as disposable infusion pumps, as well as other functions. The additional functions may be related to the therapy or medical treatment apparatus itself, such as a blood glucose measuring function for the diabetic patient controlling an ambulatory insulin pump. The additional functions may be unrelated, such as PDA, cellular telephone, or game functions. Desired remote control devices, therefore, will obviate the need for a user to carry multiple handheld devices. Preferably, the remote control devices will include power consumption regulations that prioritize power delivery for the medical controlling functions of the devices. In addition, the remote control devices will preferably include battery monitoring which substantially avoids a total loss of power for the medical controlling function. Moreover, such remote control devices will be adapted for use with multiple medical treatment apparatus, such as successive disposable infusion pumps.

SUMMARY OF THE INVENTION

In response, the present invention provides a remote control for a medical treatment apparatus that includes functions in addition to control of the medical apparatus, as desired. According to one exemplary aspect, the multi function medical apparatus remote control device includes power consumption regulations that prioritize power delivery for the medical controlling functions of the devices. According to another exemplary aspect, the multi function medical apparatus remote control device includes battery monitoring which substantially avoids a total loss of power for the medical controlling function. According to an additional exemplary aspect, the multi function medical apparatus remote control device adapted for simultaneously or serial use with multiple medical treatment apparatus, such as successive disposable infusion pumps. Also provided as an aspect of the present invention are methods for assuring proper communication between a remote control device a specific device to be controlled.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 6 is a top plan view of a packaged assembly of a medical treatment apparatus assembled in accordance with the present invention;

FIG. 6a is a top view of a remote control device of the packaged assembly of FIG. 6;

FIG. 6b is a top view of a vial of liquid medication of the packaged assembly of FIG. 6.

Like reference characters designate identical or corresponding components and units throughout the several views.

DETAILED DESCRIPTION OF EXEMPLARY EMBODIMENTS

Set forth hereinbelow are detailed descriptions of possible embodiments and examples of multi function remote control devices, medical treatment apparatus, and systems, kits and methods according to the present invention.

Figure 1:
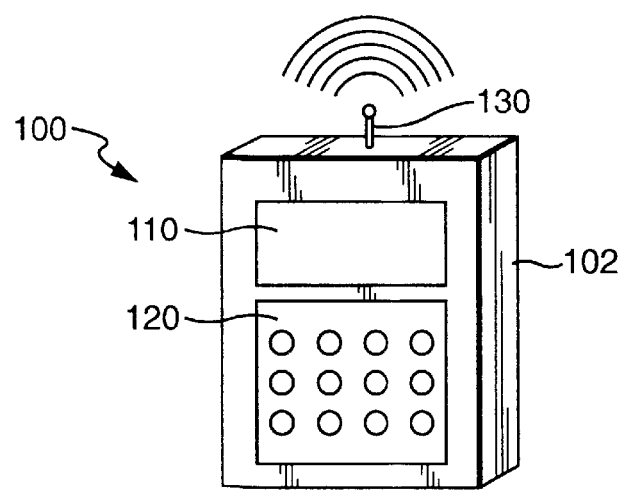
FIG. 1 is a perspective view of an exemplary embodiment of a remote control device constructed in accordance with the present invention.

Referring first to FIG. 1, there is illustrated, generally at 100, an exemplary embodiment of a multi function remote control device constructed in accordance with the present invention. The remote control device 100 includes a visual display 110, such as a liquid crystal display or LCD, that is mounted to a housing 102. Preferably, the display 110 is a touch screen display such as that included in touch screen monitors found in various equipment including the Palm Pilot® personal digital assistant manufactured by Palm Inc. of Santa Clara Calif. Mounted to the housing 102 are electromechanical switches, such as a membrane keypad 120, to allow the user to input data or activate commands. The remote control device 100 also includes means of transmitting electronic signals including antenna 130 which is shown external to the housing 102 but is preferably contained within the outer surface of the housing 102. Examples of the internal electronics and other components of the device 100 are described in detail in subsequent sections. The wireless communication is accomplished using one or more forms of electronic information transfer including radio frequency, infrared or ultrasound communications, or other forms of non-wired electronic information transfer. The device receiving the communications would include a receiving antenna, and electronics to interpret and otherwise transform the communicated data to a useful form, such as that described in subsequent figures and embodiments found herebelow.

Figure 1A:
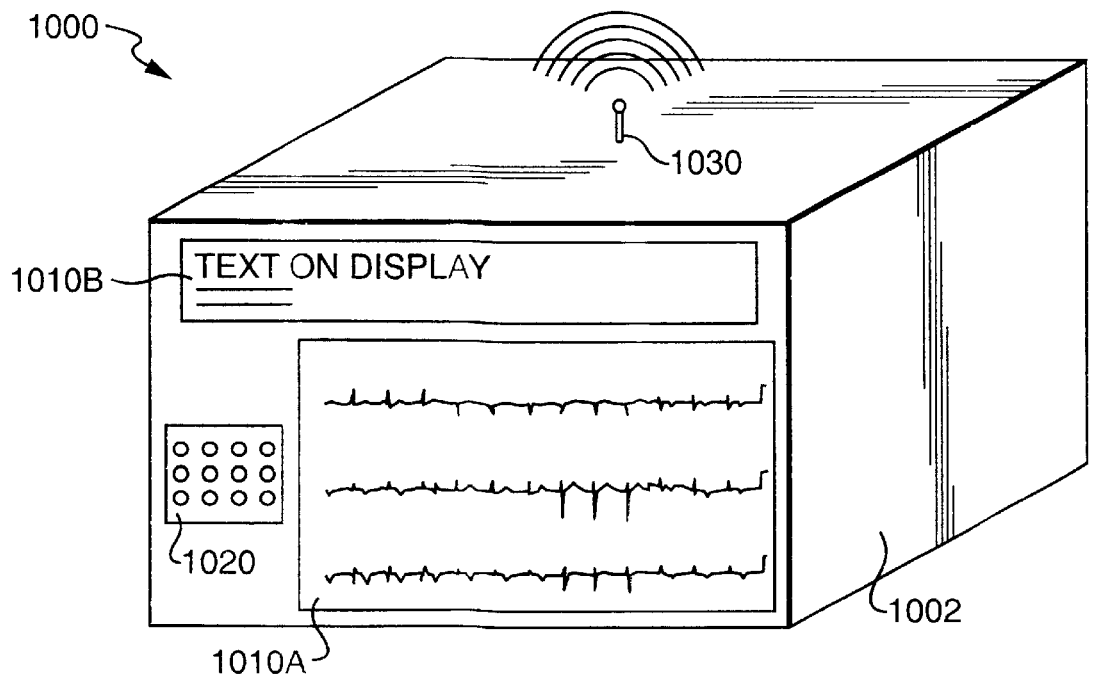
FIG. 1a is a perspective view of an exemplary embodiment of a medical treatment apparatus constructed in accordance with the present invention.

FIG. 1a depicts an example of a medical treatment apparatus 1000 of the present invention. The example is a electrocardiogram device 1000 with multiple displays, a first medical treatment apparatus display 1010A and a second medical treatment apparatus display 1010B. The first display 1010A is shown with waveforms produced by various EKG leads attached to a patient's skin (not shown) that make up a typical electrocardiogram of a heart patient with an inferior myocardial infarction. Other examples of medical treatment apparatus that can be remotely controlled include one or more of the following: external infusion pump, implanted infusion pump, pacemaker, cardiac defibrillator, neurostimulator, x-ray machine, EKG machine, diagnostic device, glucometer, blood analyzing equipment, electrocautery devices, operating room tables, visual monitors and laparoscopic remote control devices.

The medical treatment apparatus includes a housing 1002 on which is mounted various controls including electromechanical switches 1020. Also depicted in FIG. 1a is an integrated antenna 1030, shown exposed but preferably contained within the device 1000. The antenna 1030 receives signals from the remote control device 100 of FIG. 1 so that a user can adjust various parameters, request information, or otherwise command, control or communicate with the medical treatment apparatus 1000. In this embodiment, the parameters to be adjusted can include selection of a particular EKG lead to be displayed, adjustment of the display scale, or other parameters of the device 1000, for example. This remote control capability may be of great advantage when the device 1000 is close to an active x-ray, contained in the sterile field of a medical procedure, or contained in other biologically hazardous fields, for example.

The medical treatment apparatus 1000 includes internal electronics (not shown) to take the information received via the antenna 1030, interpret the data in electronic form, and adjust programming or other parameters accordingly. The remotely controllable apparatus 1000 can comprise medical devices and/or perform functions other than electrocardiogram monitoring, such as an external infusion pump, an implanted infusion pump, a pacemaker, an cardiac defibrillator, an neurostimulator, an x-ray machine, an EKG machine, blood sampling, blood analysis, a diagnostic device, a glucometer, blood analyzing equipment, an electrocautery device, an operating room table, a visual monitor, a laparoscopic device, and other medical equipment and functions.

In addition to receiving electronic wireless communication via the antenna 1030, the medical treatment apparatus 1000 may also send wireless information back to the remote control device 1000. The information can include diagnostic information, history information, equipment status information, alarm status information, or other information related to the function of the device 1000. Information can also include device specific information, such as serial number, model number or a unique identifying alphanumeric code. Information can also include confirmation that a previously downloaded transmission from the remote control device 100 was properly received, or even improperly received, thereby triggering the remote control device 100 to repeat the previous transmission of electronic data.

Each transmission of electronic data between the device 100 and the apparatus 1000 can include an identification representing the remote control device 100, the medical treatment apparatus 1000, or both. The unique identifications, which can include codes, are placed in the electronic memory of either the remote control device 100 or the medical treatment apparatus 1000 during their manufacturing process. After an initial communication between the device 100 and the apparatus 1000, either or both of the unique identifications can be transferred between the device and the apparatus, and all subsequent communications can include either or both of the unique identifications. In addition, prior to acting upon commands received from the remote control device 100, a check of proper identification can eliminate the issue of a remote control device 100 communicating with the wrong medical treatment apparatus 1000, and vice versa.

A start up or initial communication mode, therefore, is preferably conducted between the device 100 and the apparatus 1000 wherein either or both of the unique identifications is exchanged, followed by memory storage of either or both unique identifications. In addition, all subsequent communications preferably include a confirmation of the proper identification prior to acceptance of instructions. In some instances, the remote control device 100 may download a uniquely assigned identification to the medical treatment apparatus 1000, which is then stored in the electronic memory of the medical treatment apparatus 1000 to establish a unique identification for that device. Examples of identification assignment, transfer, and confirmation are described in more detail in subsequent exemplary embodiments of the present invention.

It should be understood that the remote control device 100 may include software and electronic hardware for performing other functions, such that the remote control device 100 is a "multi-function" device. Other functions can include that of a personal digital assistant, such as the Palm Pilot®. Alternatively, the other functions of the remote control device 100 can include one or more of an electronic game, a barcode reader, a television or VCR remote, or a cellular telephone, for example. Many other functions are possible.

Figure 2:
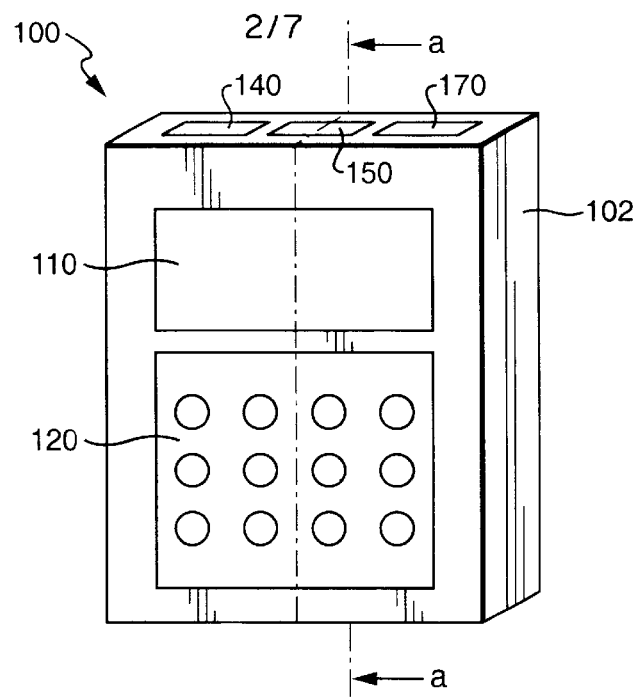
FIG. 2 is a perspective view of another exemplary embodiment of a remote control device constructed in accordance with the present invention.
Figure 2A:
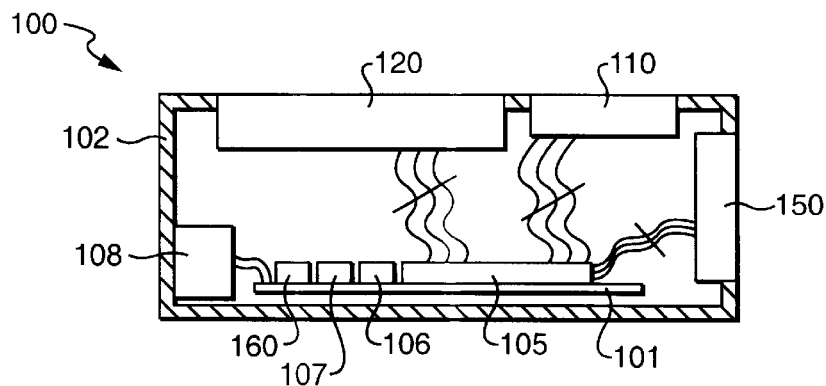
FIG. 2a is a section view of the remote control device of FIG. 2 taken along line a—a of FIG. 2.

FIGS. 2 and 2a show another possible embodiment of a remote control device 100 according to the present invention. The remote control device is similar to the remote control device of FIG. 1 such that similar elements have the same reference numerals. Internal components of the remote control device 100 are contained within a housing 102 and include a communication element 160 (referred to in appended claims as "remote" communication element) which is used to send wireless communication to the medical treatment apparatus 1000. The wireless communication may consist of electronic packets of information sent by radio frequency, infrared, ultrasound or other wireless forms of communication. Also included is a power supply 108, which can be integral to the device and rechargeable by attaching to a standard AC power converter. Alternatively, the power supply 108 may consist of standard battery technology such as nickel cadmium, alkaline, silver oxide or other batteries available at convenience and other stores, and be replaceable.

Within the housing 102 is an electronic printed circuit board 101 having electronics 105 that includes memory 107, which is shown as a separate electronic module but preferably is integral with the electronics 205. The electronics 105 also includes a microprocessor or other programmable and logic circuitry to perform programmable functions (referred to in the appended claims as "remote" processor). Other components of the electronics 105 can include digital circuitry, analog circuitry, resistors, capacitors, transistors, integrated circuits, amplifiers, additional microprocessors, logic circuitry, integrated circuits, programmable logic, analog to digital converters, digital to analog converters, multiplexors, and other semiconductor circuitry.

Preferably, a microprocessor and associated circuitry is embedded into the electronics 105 and receives programming signals from a membrane keypad 120, controls the visual display 110, and creates electronic command signals and identifiers to be broadcast in wireless form via the communication element 160. Embedded in the memory 107 of the electronics 105 or included in the microprocessor is one or more microprocessor based software programs that define, control and facilitate the operation of the device 100 in a predetermined manner.

Combined with the memory 107, which can be one or more components integrated into electronics 105, can be fixed, preprogrammed read only memory and variable, read and writeable memory. The memory 107 includes the programming necessary to support all functions of the device 100, including remote control of the medical treatment apparatus as well as the other functions such as cell phone operation, a personal digital assistant, a glucometer diagnostic function, a barcode reader, and an electronic game. The memory may also be used to store clinical therapy information, such as diabetes care guide, a troubleshooting guide and user manual for the medical treatment apparatus being remotely controlled, and a troubleshooting guide and user manual for the remote control device 100.

Also included within the housing 102 is an alarm 106 mounted to the printed circuit board 101. The alarm 106 preferably is an audio alarm such as a piezo buzzer, commercially available from Star Micronics Company, Ltd. of Edison, N.J. The alarm 106 is activated by the electronics 105 when an alert or alarm condition is encountered during operation of the remote control device 100. Alarms may be predicated by a condition in the remote control device 100 or an alarm condition detected in the medical treatment apparatus 1000 that has been uploaded into the remote control device 100. Examples of alarm conditions include detection of a malfunction, low battery conditions, or even an alarm clock function. Examples of alarm conditions uploaded from the medical treatment apparatus 1000 include low battery conditions, detection of malfunction, empty reservoir in a fluid delivery device, occlusion of flow in a fluid delivery device, out of paper condition, or out of communication range.

The communication element 160 is also shown mounted to the printed circuit board 101 and is electronically attached to the electronics 105 to feed the electronic signals, or packets of information, to and possibly from the communication element 160. Also electrically connected to the printed circuit board 101 and the electronics 105 thereon is the user interface components 110, 120.

Figure 2B:
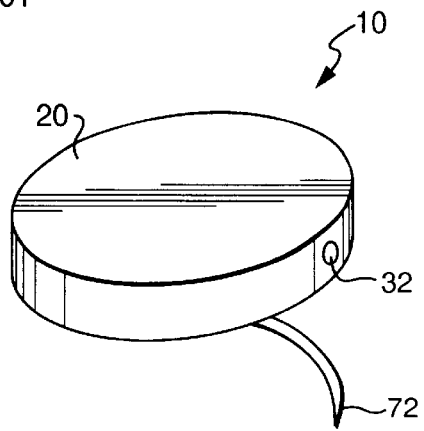
FIG. 2b is a perspective of an exemplary embodiment of ambulatory infusion device constructed in accordance with the present invention.

In one exemplary embodiment, a medical treatment apparatus of the present invention comprises an ambulatory fluid delivery device 10, as shown in FIG. 2b. The fluid delivery device 10 is for the infusion of insulin for diabetic patients, and an additional function of the remote control device 100 is a glucose measurement device, or glucometer function. In such an embodiment, the remote control device 100 includes the necessary hardware to measure blood glucose, such as that taken from a blood sample, so that a diabetic patient can avoid the need to carry multiple handheld devices (i.e., one for controlling the fluid delivery device and one for measuring blood glucose).

Thus, as shown in FIG. 2, the remote control device 100 includes a glucometer port 150, which can comprise a standard wire connector, allowing attachment to an existing glucometer device, or a more sophisticated input device for measuring blood glucose utilizing optics or sensors for analyzing blood glucose strips or blood drops. Non-invasive blood glucose technologies are commercially available or in development by various manufacturers and developers. Cygnus Corporation of Redwood City, Calif., for example, manufacturers the Glucowatch Biographer blood glucose measuring system. The glucometer port 150 can be adapted to electronically connect with a device such as the Glucowatch to transmit and receiving blood glucose information. Alternatively, the information can be communicated via wireless technologies described herein utilizing communication element 160 and a transmitting or receiving element included in the glucometer.

Alternatively, the glucometer port 150 can be replaced with another input, output or combination input and output port for allowing attachment to other devices, performance of electro mechanical functions such as bar code scanning, attachment to an information upload or download device, or performance of another function. As shown in FIG. 2a, the device 100 can also include a barcode reader port 140 for connecting to a standard barcode reader pen or gun (not shown) to simplify input of information such as drug type and concentration from a drug reservoir or vial. Alternatively, the barcode reader port 140 may include the integrated bar code reading technology and avoid the need for another device. The device 100 also includes a computer port 170 for connection to a personal computer or other computer system to upload or download information, as well as offering temporary computer control of various functions including programming or program modification of the remote control device 100 itself. The computer port 170 can include integrated wireless communication technologies to connect to a separate computer or computer network without the need for wires or mechanical connection means.

Referring to FIG. 2b, the fluid delivery device 10 is designed to be small and lightweight and includes a housing 20 and an adhesive attachment means (not shown) secured to an external bottom surface of the housing for attaching the device to the skin of a patient. Internal to the fluid delivery device 10 are a reservoir for storing the liquid medicament, a fluid dispenser for controlled fluid delivery, a communication element for receiving the wireless communications from the remote control device 100, and electronics for receiving the electronic communication and controlling the function of the device. On the outer surface of the housing 20 is included a needle insertion septum 32 to allow fluid to be placed into the reservoir of the fluid delivery device 10 via a syringe. Alternatively, the fluid delivery device 10 may be prefilled with the liquid medication at a manufacturing site prior to the device 10 being distributed to the patient or caregiver, simplifying setup and reducing cost by eliminating patient filling and obviating the need for needle insertion septum 32.

Exiting the housing 20 is the outlet of the fluid path of the device, including skin penetrating cannula 72, which is inserted transcutaneously, or through the skin of a patient into the subcutaneous tissue or other transcutaneously accessed site, such as a vein or artery, intended for the fluid delivery. Alternatively, exiting the housing 20 may be a standard Luer attachment such that a connection to a standard transcutaneous infusion set can be made.

Preferably, the fluid delivery device 10 is designed to be low cost and have limited life such as 2 to 3 days and thereafter be disposable. Such an inexpensive, disposable device is possible because the device 10 does not have an expensive, complex user interface such as electromechanical switches and visual displays, since user interface is accomplished via the remote control device 100.

The fluid delivery device 10 may be filled with insulin, and associated programming of fluid delivery device 10 and remote control device 100 sufficient to allow the sophisticated flow profiling and bolus requirements for a diabetic patient, such as insulin dependent or Type I diabetics. This patient population are required to take repeated doses of insulin just to survive, and the advantages of continuous infusion of insulin has been well demonstrated in scientific studies.

In the case where the remotely controlled medical treatment apparatus is a mass produced product, such as the disposable infusion pump 10 described above, the remote control device 100 may communicate with numerous infusion pumps 10 over a period of time. For each new infusion pump 10 placed into operation by a user, a unique identification of the fluid delivery device 10 can be uploaded into the remote control device 100 and a unique identification of the remote control device 100 can be downloaded into the fluid delivery device 10.

In a preferred embodiment, the disposable fluid delivery device 10 does not include a unique identification, as this may add cost to the manufacturing process. Instead, at first communication with a new fluid delivery device 10, the remote control device 100 is programmed to download a unique identification to the new fluid delivery device 10, which in turn is programmed to store the unique identification in its internal memory for the remainder of its life. All subsequent communications between the remote control device 100 and the fluid delivery device 10 then include the unique identification previously downloaded to assure secure and proper communication between the remote control device 100 and the specific delivery device 10.

For example, the memory 107 of the remote control device 100 automatically assigns a new, unique identification to each new pump 10 at the initial communication, and includes the unique identification in each communication with the pump to prevent the pump from receiving commands from other remote control devices that may be in proximity with the pump 10. The initial communication and exchange of the unique identifications can be prompted by a user, or the remote control device 100 and the fluid delivery device 10 can be programmed to automatically exchange identifications upon initial communications.

Figure 3:
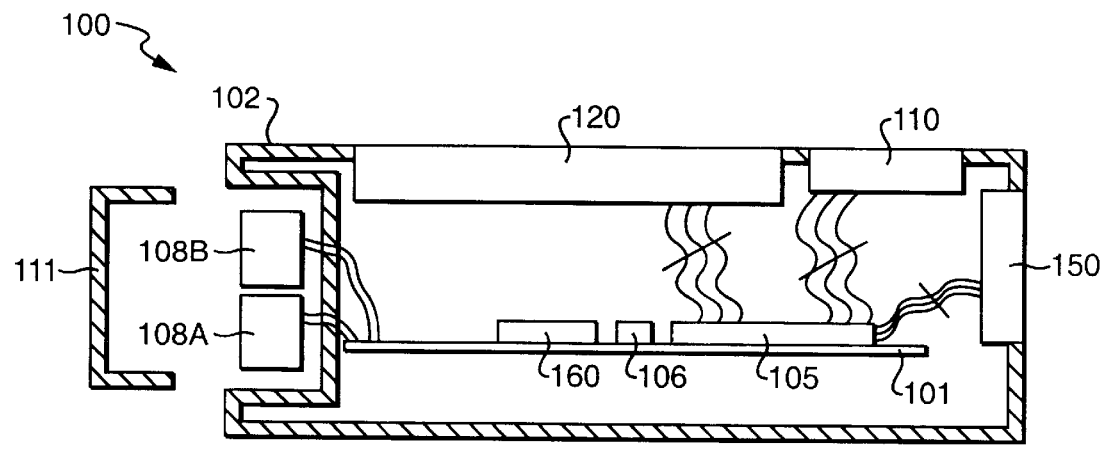
FIG. 3 is a sectional side view of another exemplary embodiment of a remote control device constructed in accordance with the present invention.

FIG. 3 depicts a cross sectional side view of another possible embodiment of a remote control device 100 of the present invention. The remote control device is similar to the remote control device of FIG. 2 such that similar elements have the same reference numerals. The remote control device 100 of FIG. 3, however, further includes multiple power supplies to prevent inadvertent power outage for portions of the device 100 relating to control of a medical treatment apparatus.

Removable from the housing 102 is a battery door 111, which allows access to first power supply 108A and second power supply 108B, which can comprise replaceable batteries. Preferably, at least one of the first power supply 108A and the second power supply 108B is always used to power each function of the remote control device 100. When the energy remaining in the first power supply 108A (referred to in the appended claims as "general purpose power supply") decreases to a certain predetermined level or other means of determining remaining energy life, the second power supply 108B (referred to in the appended claims as "dedicated power supply") is utilized for power. The first power supply 108A can continue to be depleted or may be electrically disconnected or otherwise unused. The second power supply 108B is not used to supply power for each function, but a reduced number of functions including remote control of a medical treatment apparatus. Preferably, the second power supply 108B provides power only to the remote control function.

Determination of remaining energy level for each power supply 108A, 108B can be performed by electronic voltage detectors, electronic current detectors and integration of values of current used, time duration measurements, measurements of types and duration of use, a combination of any of the aforementioned techniques along with other energy consumption and battery level detection methods known to those of skill in the art. Power supply 108A, 108B selection based on power consumption management can be accomplished with electronic switches such as transistor or other semiconductors switching circuits.

It should be appreciated that the two power supplies 108A, 108B can provide power to separate specific functions, or there may be particular functions that are provided power by both power supplies. Particularly, the function of controlling a medical treatment apparatus can be powered by both power supplies 108A, 108B, while other functions are limited to just one of the two supplies 108A, 108B, for the purpose of insuring continued, non-interrupted remote control function. In a particular embodiment, the first power supply 108A supplies power to all functions of the device 100, and the second power supply 108B only supplies power to the medical apparatus controlling functions and becomes activated only when the first power supply 108A is depleted to a predetermined level. Each power supply 108A, 108B can be a battery, or other energy storage means such as a capacitor, can be user replaceable, or can be integral to the device and rechargeable with standard recharging means. In one possible embodiment, the second power supply is provided as a capacitor or battery that is not user replaceable, is enclosed within the housing 102, and is not accessible via removal of a battery door.

In any event, the dual power supply configuration allows the remote control device 100 to prioritize providing power to support the remote control of a medical apparatus versus other user supportive functions, such as a cellular phone function. Since it may be greatly preferred to allow down time with the cellular function versus any down time with the control of the medical treatment apparatus, the dual power supply control functions described herein avoid a user inadvertently or accidentally depleting a battery supply using a function such as a phone call and then being unable to control their medical apparatus.

It is a great advantage for the user to be able to combine a remote control of a medical apparatus with other functions such as cellular phones, personal digital assistant, or other handheld electronic device. However, if use of the non-medical function depletes the battery to a low enough level to prevent control of the medical apparatus, the multi function device may lose its appeal. The power supply control circuitry described herein, therefore, prevents non-medical usage of remote control device 100 that would deplete the batteries to a point of loss of the medical apparatus remote control function.

Figure 3A:
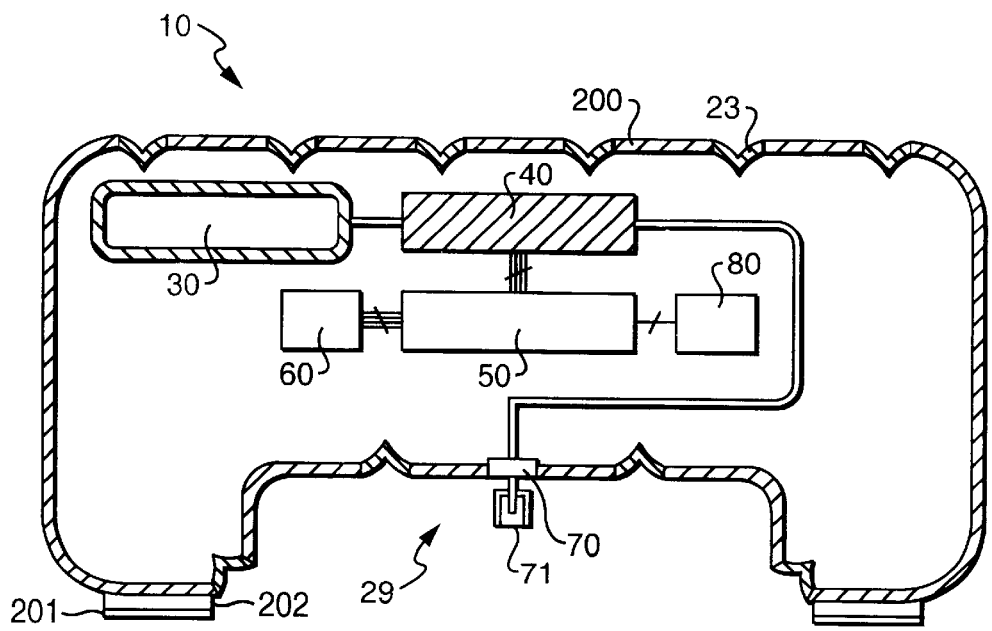
FIG. 3a is a sectional side view of another exemplary embodiment of an ambulatory infusion device constructed in accordance with the present invention.

FIG. 3a shows a fluid delivery 10 to be remotely controlled by a remote control device 100 of the present invention. The fluid delivery device of FIG. 3a is similar to the fluid delivery device of FIG. 2b. The fluid delivery device 10 includes recessed housing 200 which includes a recessed surface 29 positioned within a continuous ring adhesive layer 201. Located beneath housing adhesive layer 201 may be secondary housing adhesive layer 202 such that if the housing adhesive layer 201 loses sufficient adhesive properties and is removed, the secondary adhesive layer 202 is available to attach, or reattach, the fluid delivery device 10 to skin of a patient. Preferably, the size of the fluid delivery device 10 is small to allow comfortable adhesive attachment to the patient's skin. Based on the size and shape of recessed housing 200 it may be desirable for the outer shell to flex after adhesive attachment to the patient's skin. Included at various locations along recessed housing 200 are housing hinged sections 23, to allow flexing.

Included within the housing 200 is a reservoir 30 which is designed and constructed to be compatible with the liquid medication, such as insulin, to be infused. In a preferred embodiment, the reservoir 30 is prefilled with the liquid medication, however the entire reservoir can be inserted by the user if in the form of a prefilled cartridge, not shown, or the fluid delivery device 10 may include medication fill means, such as a needle penetrable septum in fluid communication with the reservoir 30, also not shown. The reservoir 30 is in fluid communication with a dispenser 40, which is used to precisely control the amount of fluid to exit the fluid delivery device 10 via exit port assembly 70. FIG. 3a depicts an exit port assembly 70 including a standard attachment such as a Luer connector 71 which can be attached to a transcutaneous infusion set (not shown) for transcutaneous delivery of the liquid medication. Alternatively, the Luer connector 71 can be replaced with a transcutaneous cannula assembly that is integrated into exit port assembly 70 and obviates the need for the transcutaneous infusion set.

The dispenser 40 controls fluid flow from the reservoir 30 to the exit port assembly 70, and can comprise a linear or rotary peristaltic pump if the reservoir 30 is not pressurized. Alternatively, the dispenser 40 can comprise an electrodynamic pump, a displacement pump or other fluid pumping mechanism. The dispenser 40 can be combined with a separate metering element to achieve the proper volume of fluid to be infused, or the dispenser 40 can be adapted to independently infuse the correct volumes.

If the reservoir 30 is pressurized, by a compressing member or by being enclosed in a gas pressurized chamber for example, the dispenser 40 can be adapted to simply meter the fluid from the reservoir. The dispenser 40 can then include an accumulator chamber and valves before and after the accumulator chamber to dispense fixed pulses of fluid. Alternatively, the dispenser 40 can be adapted to control flow rate via orifice constriction and expansion.

Still referring to FIG. 3a, an electronic microcontroller 50 (referred to in the appended claims as a "local" processor) is used to electronically control the dispenser 40. The dispenser 40 can include electrically driven propulsion means, electrically activated remote control devices such as piezo valves or solenoid actuators, motors or micro motors, or other electromechanical components requiring electrical signals for activation, power or both. Powering the dispenser 40 and the electronic microcontroller 50 is a power supply 80, which is preferably a battery. If the fluid delivery device 10 is a low cost disposable advice, the power supply 80 is preferably integral to the fluid delivery device 10 to thereby avoid the need for a user to purchase and insert batteries.

The fluid delivery device 10 of FIG. 3a is controlled by a remote control device, such as the remote control devices 100 of FIGS. 2 and 3, via wireless electronic signals sent by the remote control device and received by a communication element 60 (referred to in the appended claims as a "local" communication element), shown in FIG. 3a. Preferably, the fluid delivery device 10 is a low cost disposable insulin pump, and includes no user interface components and can only be interfaced with by a user via a remote control device.

In one embodiment, the communication element 60 both receives and transmits electronic signals to the remote control device 100. Information transmitted by the fluid delivery device 10 may include alarm conditions, programming history, infusion history, confirmation of programming, handshaking or other communication confirming codes, or other electronic controls or information transfer. Information can be transferred with standard wireless technologies such as radio frequency or infrared, and include standard handshaking or other communication confirmation protocols such as those employed in commercially available modems and fax machines.

Figure 4:
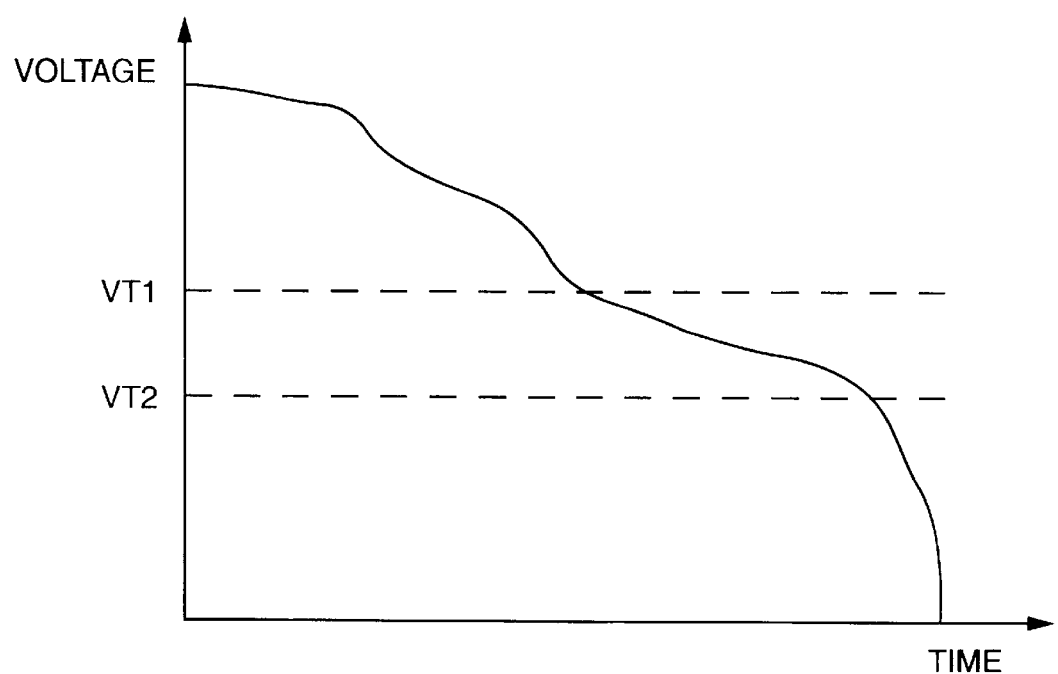
FIG. 4 is a chart illustrating voltage decay over a period of time and low battery level thresholds for a remote control device constructed in accordance with the present invention.

FIG. 4 is a graph of voltage versus time of a power supply for a handheld electronic device. The decay curves of voltage over time for typical use or typical battery drain is shown. Referring also to FIG. 3, such measurements of the general purpose power supply 108A can be used to by the remote control device 100 to determine when the dedicated power supply 108B is used to supply power to the remote control device 100. For example, the internal electronics 105 can measure the energy level, such as a voltage level, of the first power supply 108A and when the level decreases below a certain value, employ the second power supply 108B.

In FIG. 4, the voltage curve is for the general purpose power supply 108A of FIG. 3. A second voltage threshold VT2 is shown in FIG. 4 and represents a predetermined energy level at which the dedicated power supply 108B is utilized. The measurement electronics 105 may include means of detecting when the voltage of the general purpose power supply 108A first drops below the second voltage threshold VT2, such that if the voltage increases above the second voltage threshold VT2 thereafter, the battery control conditions remain unchanged so that the dedicated power supply 108B remains connected. Such a method of differentiating a voltage level slightly above a threshold if the level had previously decreased below the threshold is known as a hysteresis function or method. Once a threshold level is crossed, minor measurement perturbations above the threshold do not change the resulting actions from the initial crossing. When the voltage exceeds the threshold by a more significant, preset level, such as that caused by new battery replacement or recharge, the actions are reversed or a new action performed.

An alternative to the dual power supply construction presented in FIG. 3 and discussed above, includes the creation of two preset energy thresholds for use with the single power supply 108 illustrated in FIG. 2a. The remote control device 100 further includes means for measuring a threshold such as a first voltage threshold VT1, illustrated in FIG. 4. When the energy level in the single power supply 108 decreases to below the first voltage threshold VT1, functions of the device 100 not related to the remote control of the medical treatment apparatus are deactivated or shutdown.

For example, a non-medical function such as cellular telephone use, may be of a de-prioritized nature as compared to control of a medical treatment apparatus such as a fluid delivery device for the delivery of insulin to a diabetic patient. Therefore, the remote processor 105 is programmed to shut down the cellular telephone function of the remote control device 100 when the available power of the single power supply 108 decreases below the first voltage threshold VT1 in order to allow one or more hours of control of the fluid delivery device.

In addition, a possible embodiment of the remote control device 100 can include an override function that allows continued use of the non-medical control function(s) if desired by a user. In cases of emergency, for example, the cellular phone function of the device 100 may be of such importance that continued use of the phone function at the risk of deactivation of the medical control function due to depletion of the single power supply 108 may be acceptable. In such an embodiment, the remote control device 100 might require the user to override the deactivation by confirmation via the keyboard 120 or other user input means of the device 100 to reactivate the phone function. The override may be temporary or permanent, and may trigger a second level of remaining energy level thresholds (e.g., VT2) to be employed for the deactivation of the phone function when the available power of the single power supply 108 decreases below the second voltage threshold VT2.

The remote control device 100 may include means of alerting the user prior to deactivation of any functions. This alert may be accomplished with audio or visual information made available to the user by detection of particular energy states of the one or more power supplies. For example, a voltage threshold just above the first voltage threshold VT1 may cause the alert condition to occur, thus notifying the user that certain functions are near deactivation, similar to a low battery warning condition found in many battery powered devices. In addition, multiple thresholds can be detectable by the electronics of the remote control device 100 such that one or more low battery conditions, as they relate to individual or groups of specific functions, can be used to selectively deactivate individual or groups of specific functions in a prioritized manner. For example, a remote control device 100 that includes medical treatment apparatus control, cellular telephone function and personal digital assistant function, may include thresholds for all three stated functions and deactivate the PDA function first and then the cellular function prior to the medical treatment apparatus remote control device function.

It should be considered in the scope of this application that there are various techniques for determining the amount of energy remaining in one or more power supplies. Voltage detection is common and the energy dissipation curves of batteries of various technologies can be predicted quite reliably. Other techniques can be used in conjunction with or independent of voltage detection without departing from the spirit of this application. Examples of one or two power supply embodiments have been described, however three or more power supplies can be used to achieve similar outcomes, and a single power supply may consist of more than one battery, connected in series or in parallel or both. In addition, multiple energy thresholds can be measured in any or all of the power supplies to change the status of function availability. In other words, one or more batteries can be employed utilizing one or more remaining energy measurements, preferably voltage thresholds. Based on these thresholds, additional power supplies can be brought on line and or particular functions made no longer available or deactivated, to insure continued operation of the medical apparatus apparatus control function.

In addition to discreet energy level measurements, such as voltage level measurements, a history of activity potentially including current measurements, history of battery replacements and measurements, and other multiple information data analysis can be used, integrated, or otherwise analyzed to determine which functions to enable and disable, or how to distribute power among the functions.

Figure 5:
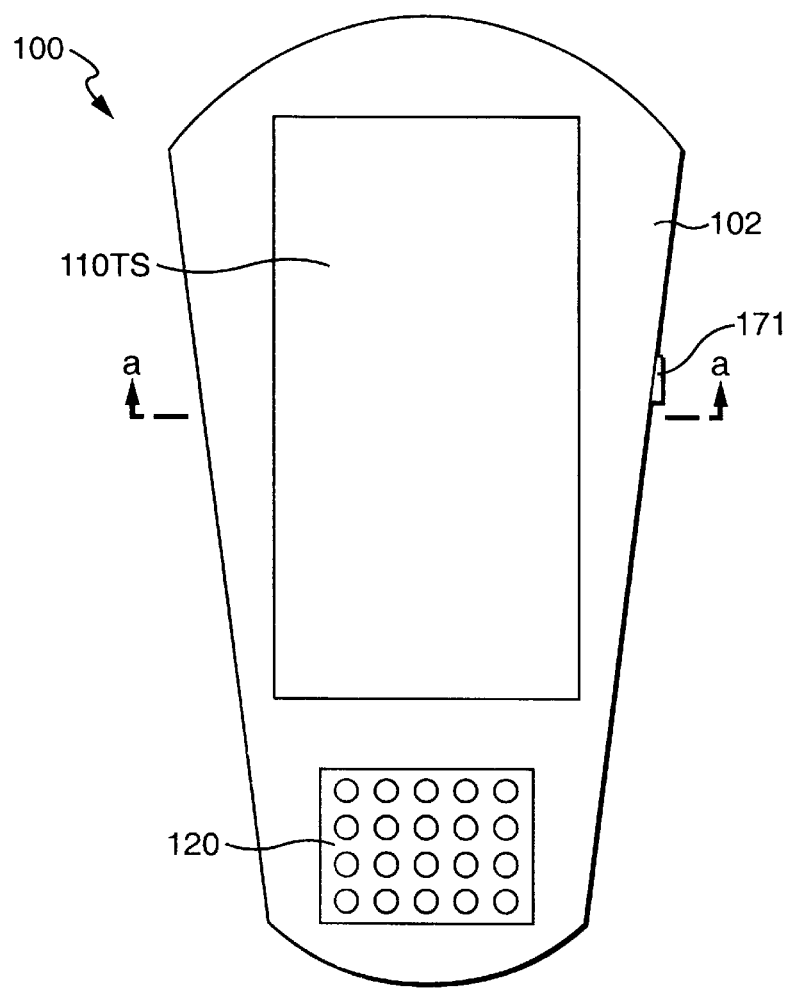
FIG. 5 is a top plan view of a further exemplary embodiment of a remote control device constructed in accordance with the present invention.
Figure 5A:
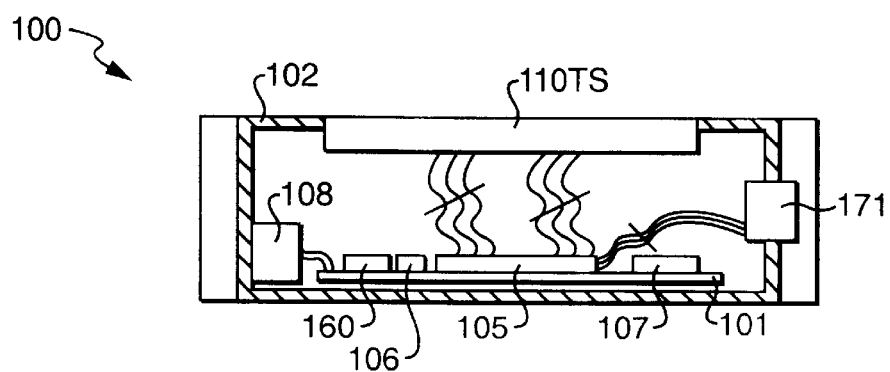
FIG. 5a is a sectional view of the remote control device of FIG. 5 taken along line a—a of FIG. 5.

Another exemplary embodiment of a remote control device 100 of the present invention is shown in FIGS. 5 and 5*a*. The device of FIGS. 5 and 5*a* is similar to the device of FIGS. 2 and 2*a* such that similar elements have the same reference numerals. The device of FIGS. 5 and 5*a*, however, includes a "touch screen" display 110TS for allowing user input as well as for displaying information.

Also included in the remote control device 100 of FIGS. 5 and 5*a* is an electronic communication port 171. The port 171 can be a simple modem for connection to an outside computer or internet system via a phone line, or an Ethernet connector for connection to a network, the internet, or other wired electronic communication channel. The communication port 171 can facilitate other forms of electronic information upload or download, most particularly information which can be sent to the user to help manage, troubleshoot and otherwise use the medical treatment apparatus being controlled. The information can be uploaded or downloaded from a clinician or other health care giver, the manufacturer of the remote control device 100, or the manufacturer of the medical treatment apparatus being remotely cointrolled.

Alternatively, all of these upload and download communications can be accomplished via wireless technologies accepted by communication element 160 contained within the remote control device 100. In this wireless scenario, communication can be sent via satellite or other global or near global communication, updating each applicable remote control device 100 with new programming information, text or user manual information, or other data stored within the memory 107. The information can be received by communication element 160 whose primary function is to send, and potentially receive wireless communications to medical apparatus treatment apparatus 1000.

FIG. 6 shows a packaged assembly 350 which includes a fluid delivery device 10 similar to the fluid delivery devices of FIGS. 2*b* and 3*a*. The fluid delivery device 10 is packaged in an assembly tray 353, which can be constructed of a sterilizable material such as PETG, or polycarbonate, and is seal with an assembly lid 352, which can be constructed of sterilizable material such as Tyvek® wrap material supplied by DuPont Corporation of Wilmington, Del. The assembly lid 352 may include an adhesive on its bottom surface to facilitate sealed attachment to the assembly tray 353.

The sealed tray construction allows the fluid delivery device 10 to be sterilized utilizing various methods, including ethylene oxide sterilization. In one possible embodiment, the fluid delivery device 10 of the packaged assembly 350 can include an integral transcutaneous infusion set. At least the transcutaneous infusion set and fluid path portions of the device 10 are sterilized to prevent contaminants from passing through the skin of a patient using the device 10.

Also shown in FIG. 6, the fluid delivery device 10 is provided with an information barcode 26. Such an information barcode 26 may be utilized by various systems for cataloging or otherwise recording information about the fluid delivery device 10. The remote control device 100 of FIG. 6*a* can be provided with a bar code reader function, and can be programmed to upload the information barcode 26 data to perform an initialization function described hereabove. The information barcode 26 data can be unique for each fluid delivery device 10 and include a unique fluid delivery device identification, or other unique and non-unique information such as manufacturing date, serial number, type of medication preloaded, concentration of medication, physician identification, patient identification, or other clinical or non-clinical information. The use of information barcode 26 containing unique device information, versus including such unique information in the electronic memory of the fluid delivery device 10 may be more efficient and cost effective for mass production of the fluid delivery device 10, especially in designs and constructions where the device is to be of extreme low cost for limited life or disposable use.

A preferred packaging construction to the tray and lid described above would be a sealable pouch, common to the medical apparatus industry. The pouches usually consist of a rectangular piece of breathable material such as Tyvek, which is sealed to a piece of clear flexible plastic, such as thin Mylar. The pouch construction can be sterilized in similar fashion to the tray and lid packaging, and is generally of less cost to manufacture without providing the rigid protection of the tray packaging.

FIG. 6b depicts a top view of therapeutic fluid supply 250. Therapeutic fluid supply 250 may include a glass or plastic vial, and may be filled with various types of one or more liquid medications such as insulin. The therapeutic fluid supply 250 may be loaded, like a cartridge, into a properly designed and adapted fluid delivery device 10, or the contents of therapeutic fluid supply 250 may be transferred, through interlocking fluid connection or via syringe and needle, into fluid delivery device 10 at a integral injection port, not shown. Alternatively, fluid delivery device 10 may be prefilled with the liquid medication obviating the need for therapeutic fluid supply 250.

Various ways of combining devices of the present invention into appropriate infusion kits can include packaging multiple units of one type of device with a single other type of device. For example, a single remote control device 100 of the present invention can be provided as a kit with thirty to one hundred low cost, disposable fluid delivery devices 10 of the present invention. Typical kit configurations include a single remote control device 100 packaged with multiple delivery device packaged assemblies 350, each containing fluid delivery device 10. If the fluid delivery device 10 is not filled with liquid medication, therapeutic fluid supply 250 are also packaged in the infusion kit. In addition to the above components or products, other components or products may be packaged in the infusion kit such as user instructions, batteries for the remote control device 100, multiple batteries for the fluid delivery devices 10, syringes, needles, transcutaneous penetration site preparation materials, and other peripheral devices. In addition, blood glucose measuring supplies such as finger prick devices, test strips, diagnostic devices such as glucometers, and other blood glucose measurement accessory devices may be supplied in the kit. One or more backup remote control devices 100 can also be included with the kit. Many variations of kits are possible.

Figure 7:
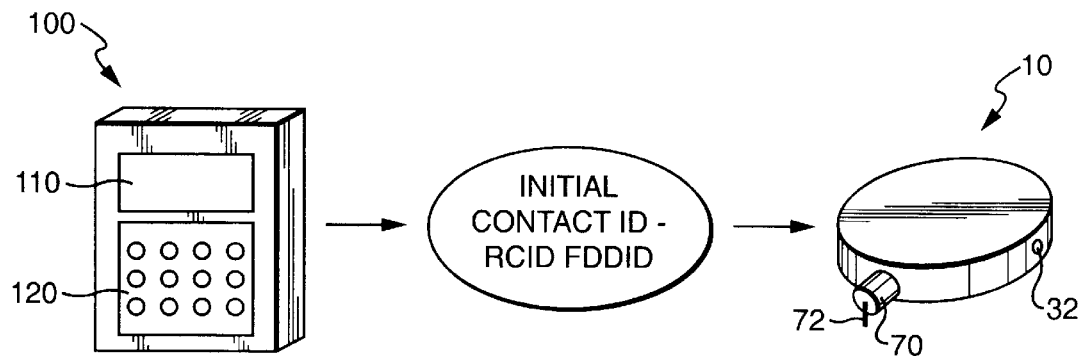
FIGS. 7, 7a and 7b are perspective views illustrating an exemplary embodiment of a method of wireless communication according to the present invention conducted between a remote control device and a fluid delivery device of the present invention.
Figure 7A:
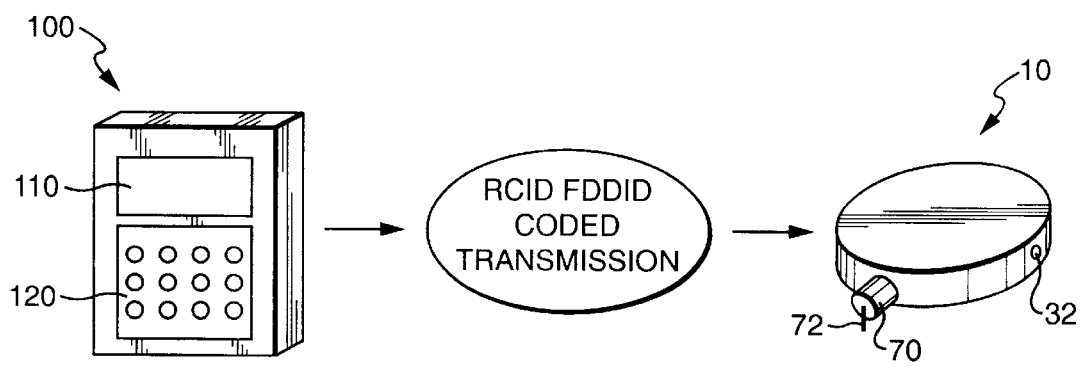
Figure 7B:
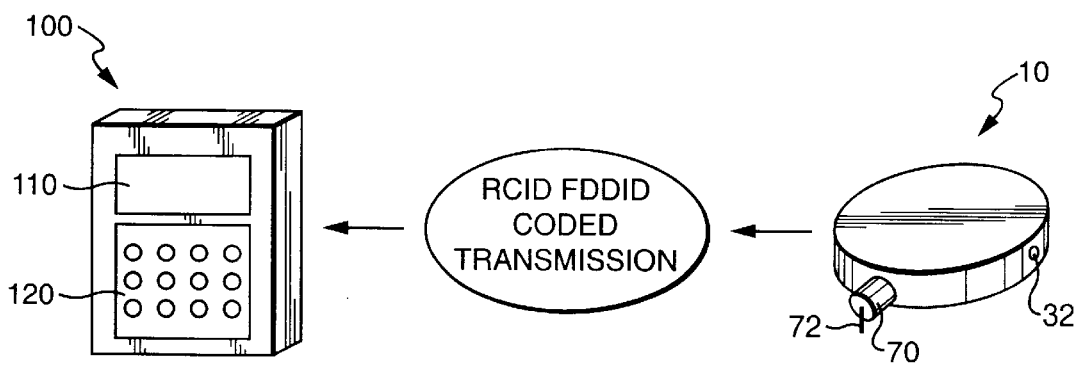

FIGS. 7, 7a and 7b depict diagrammatic views of an embodiment of a remote control device 100 communicating with an embodiment of a fluid delivery device 10 or the present invention. FIG. 7 depicts an initial communication between the remote control device 100 and the fluid delivery device 10 wherein the remote control device 100 sends a wireless electronic information signal to the fluid delivery device 10. The internal electronics of the fluid delivery device are programmed to detect an initial communication, and from then on only accept communications that include information different than information contained in the initial communication. The initial communication may include codes that signify the initiation, and subsequent communications may include codes that not only signify not being the initial communication, but also include information calculated, uploaded, downloaded or otherwise determined during or as a result of the initial communication.

In a preferred embodiment, all fluid delivery device 10 internal programming by manufacturing is standardized, or non-unique, to reduce manufacturing costs. At the initial communication with the remote control device 100, a unique identification is transmitted to the fluid delivery device 10, received by the fluid delivery device 10, and stored in the memory of the fluid delivery device 10. In a preferred embodiment, the fluid delivery device 10 can transmit signals as well as receive, to provide two-way communication with the remote control device. Receipt of the assigned fluid delivery device identification can be transmitted by the fluid delivery device 10 to the remote control device 100 to confirm the initialization and subsequent communications.

The remote control device 100 memory may communicate with many fluid delivery device 10 over the life of the remote control device 100, and thus a matrix of fluid delivery device identifications would be maintained in the memory of the remote control device 100 to avoid duplication of identifications. In addition, the remote control device 100 may transmit a unique identification for itself to the fluid delivery device 10, to insure that in all subsequent communications, signals are received by the correct remote control device. For practical purposed, the unique identification downloaded to the fluid delivery device 10 may include a unique prefix, suffix or other part identifying the remote control device in a unique way, as well as a unique additional identification code, whereby the combined codes is the unique identification for the fluid delivery device, and the entire unique code is checked at each transmission to insure proper correlation of both devices. In the preferred embodiment in which the fluid delivery device 10 can transmit information to the remote control device, the unique identification can be included in fluid delivery device 10 transmitted communications as well.

In an alternative embodiment, the fluid delivery device 10 may be manufactured with a unique identification, such as a serial number, in its electronic memory. In this configuration, the fluid delivery device 10 would transmit the unique identification to the remote control device 100 in the initial communication in addition to the remote control device 100 transmitting its unique identification to the fluid delivery device 10, each device holding both unique codes in electronic memory, and checking for proper device communication at each transmission.

FIG. 7 depicts the initial communication between devices where a remote control device identification "RCID", and a fluid delivery device identification "FDDID" are transmitted from remote control device 100 to the fluid delivery device 10. As described hereabove, the unique identification can simply be a combination of the two device identifications with or without additional coded information. The fluid delivery device identification FDDID can be generated by the remote control device 100 or already preprogrammed into fluid delivery device 10 at the time of manufacturing. In this instance, the code may be included in random access or RAM memory or in read only memory or ROM memory. In the case where the unique identification is downloaded from the remote control device 100, the unique identification would be stored in RAM. Alternatively, a label containing a barcode, as described hereabove, can be read by the remote control device 100 and subsequently downloaded into the electronic memory of the fluid delivery device 10.

FIG. 7b depicts a subsequent electronic, wireless communication including the remote control device identification RCID and including the fluid delivery device identification FDDID in addition to other programming, control, command or other information sent from the remote control device 100 to fluid delivery device 10. Prior to action related to the command codes sent, a check would be performed to confirm completion and accuracy of the message, using checksum or other appropriate techniques, as well as a check that the proper remote control device 100 had sent the information to the proper fluid delivery device 10. After acceptable confirmations, a return signal may be sent to acknowledge acceptance, and then appropriate actions would take place in the fluid delivery device 10.

FIG. 7c depicts a subsequent electronic, wireless communication including the remote control device identification RCID and including the fluid delivery device identification FDDID in addition to other programming, control, command or other information sent from the fluid delivery device 10 to remote control device 100. Prior to action related to the command codes sent, a check would be performed to confirm completion and accuracy of the message, using checksum or other techniques known to those of skill in the art, as well as a check that the proper fluid delivery device 10 had sent the information to the proper remote control device 100. After acceptable confirmations, a return signal may be sent to acknowledge acceptance, and then appropriate actions would take place in the remote control device 100.

In a preferred embodiment, the fluid delivery device 10 is an insulin delivery device for diabetic patients. The fluid delivery device is disposable, used by the patient for three or less days, and requires the remote control device 100 for programming and use. It is imperative that proper communications are confirmed including confirmation that the proper remote control device 100 is commanding the proper fluid delivery device 10. These patients may be part of patient groups, attend diabetes conferences, or otherwise be in the presence of one or multiple patients who utilize the same system. Protocols such as that disclosed in this application are imperative to prevent undesired programming changes of any type. In addition, the remote control device 100 and or fluid delivery device 10 may include a proximity alarm or alarms such that when the distance between the remote control device 100 and fluid delivery device 10 exceeds a particular amount, one or both devices produce an audible and or tactile, such as vibrational, alarm.

The unique identification of either device may include alpha numeric designators or simple binary digits, or a binary representation of a more sophisticated code. The transmissions may include digital or more sophisticated waveforms, each including the unique codes representing either or both the medical treatment apparatus devices. The fluid delivery device 10 programming can be made such that after the initial communication with a remote control device 100, the fluid delivery device will only accept command codes from transmissions received with that remote control device 100 unique identification, remote control device identification RCCID. Alternatively, the fluid delivery device 10 programming may allow control from multiple remote control device 100, with more complex acceptance schemes. The remote control device 100 may include programming and unique identifications that identify master remote control devices, or remote control devices that are used for diagnostic, troubleshooting, clinician, or other purposes. Control of a fluid delivery device 10 by a remote control device 100 that did not initialize that particular fluid delivery device 10 may involve special passwords, keys, or other special functions or actions to allow the fluid delivery device 10 to accept the commands from the new remote control device 100. Conversely, the remote control device 100 will include programming to allow it to communicate with many fluid delivery device 10, however, perhaps not more than one at a time. The remote control device 100 may include programming such that after an initial communication, only that particular fluid delivery device 10 can be controlled until another initial communication information transfer is performed with a new fluid delivery device 10, after which the previous fluid delivery device 10 may or may not be able to be controlled by that remote control device 100. Obviously, it may be desirable to obtain information from a previously used fluid delivery device 10, so programming may allow information transfer, or upload from the previously used fluid delivery device 10 to the remote control device 100 but prevent actual infusion programming or other controls.

The remote control device may include programming or command sets which are available only to certain users such as the patient, clinician, diagnostic technician, clinical technician, product technician, or other unique user. Each of the functions may be password or otherwise controlled to limit access. In all instances, the remote control device 100 will include at least a transmitter, and a medical treatment apparatus, such as the fluid delivery device 10, will include at least a receiver. In a preferred embodiment, remote control device 100 further includes a receiver, and the fluid delivery device 10, further includes a transmitter.

Various methods of using remote control device 100 are included in the present invention and described above. The method of programming the fluid delivery device 10 with remote programmer 100 as well as control of other forms of medical treatment apparatus 1000 are described. Also relevant is the ability to update the internal programming of either the fluid delivery device 10 or the remote control device 100 by the corresponding device. Methods of creating and mapping unique alphanumeric identifications for a medical treatment apparatus, such as the fluid delivery device 10 of the present invention, and the remote control device 100 have been described.

While the majority of description for a medical treatment apparatus have regarded a fluid delivery device 10, many other types of medical apparatuses are applicable for use with a remote control device of the present invention 100. The value of the multi function remote control 100 is enhanced in situations where the user is more likely to carry the remote control device in their daily routine, or as part of their job. This condition is obvious with the diabetic patient for continuous infusion of insulin, but also found in patients and hospital workers who need to control medical treatment apparatus for a long portion of their day, potentially their working day. The advantage of other multiple uses makes the requirement of carrying and otherwise maintaining the remote control device seem less burdensome, and may reduce the need to carry around a separate device such as a PDA, cellular phone or other handheld electronic device. The methods and design features described in this application that relate to disposable fluid delivery devices, can be applied to non-disposable fluid delivery devices as well as other medical apparatus and should not in any way limit the scope of the remote control device 100 or the applicable systems.

Although exemplary embodiments of the invention have been shown and described, many changes, modifications and substitutions may be made by those having ordinary skill in the art without necessarily departing from the spirit and scope of this invention. For example, a power supply has often been described as a battery, such as a silver oxide battery. If two or more silver oxide batteries were connected in series to increase voltage or if placed in parallel to increase the available supply of current, they may be considered as a single power supply. Combinations of batteries, capacitors and other energy storage devices in series or parallel, acting either as a single power supply or as multiple power supplies can be made without departing from the scope of this application. Also, various means of power or energy level detection have been described, such as voltage level detection, but various other means of measuring, monitoring or otherwise calculating remaining energy can be used. Also, various methods of creating and storing electronic unique identifying codes have been described, however other means of coding transmissions to create unique identifications that can be uploaded and downloaded to accomplish confirmed communication between the remote control device 100 and medical treatment apparatus 1000 may be employed.

Also, the fluid delivery device of this invention is intended to be low cost, light weight, simple to use and potentially disposable by removing a majority of the user interface, including electromechanical switches, from the fluid delivery device, and including a separate remote control device to replace those functions. A reservoir, fluid dispenser, transcutaneous fluid administration means, solid state electronics and wireless communications are included in the fluid delivery device to perform its intended function. While various means of reservoir construction, pressurization means, fluid pumping means, fluid metering means, transcutaneous delivery, electronic control and wireless communications have been discussed in this application, alternatives to each of these areas can be made without departing from the spirit of the invention.

In addition, where this patent application has listed the steps of a method or procedure in a specific order, it may be possible (or even expedient in certain circumstances) to change the order in which some steps are performed, and it is intended that the particular steps of the method or procedure claims set forth herebelow not be construed as being order-specific unless such order specificity is expressly stated in the claim.

What is claimed is:

1. A system for providing medical treatment to a patient, comprising:
    A) a medical treatment apparatus including,
        a local processor, and
        a local communication element connected to the local processor;
    B) a remote control device separate from the medical treatment apparatus and including,
        a remote processor,
        user interface components connected to the remote processor,
        a remote communication element connected to the remote processor and adapted to communicate with the local communication element of the medical treatment apparatus in a wireless manner such that information can be transferred between the local processor and the remote processor, and
        at least two separate power supplies connected to the remote processor wherein the separate power supplies include a general purpose power supply and a dedicated power supply and the remote control device is adapted to use the dedicated power supply only for a subset of the functions of the remote.

2. A system according to claim 1, wherein the medical treatment apparatus includes a unique identification included in all communications between the medical treatment apparatus and the remote control device.

3. A system according to claim 1, wherein the remote control device includes a unique identification included in all communications between the medical treatment apparatus and the remote control device.

4. A system according to claim 1, wherein the medical treatment apparatus comprises one of an external infusion pump, an implanted infusion pump, a pacemaker, a cardiac defibrillator, a neurostimulator, an x-ray machine, an EKG machine, a diagnostic device, a glucometer, a blood analyzer, an electrocautery device, an operating room table, a monitor, and a laparoscopic controller.

5. A system according to claim 1, wherein the remote control device is also adapted to function as at least one of a cellular phone, a personal digital assistant, and an electronic game.

6. A system according to claim 1, wherein the remote control device further includes electronic memory storing a user manual for the medical treatment apparatus.

7. A system according to claim 1, wherein the wireless communication between the remote control device and the medical treatment apparatus is radio frequency signals.

8. A system according to claim 1, wherein the remote control device further includes an alarm connected to the remote processor and the remote processor is programmed to activate the alarm upon a measured power level of a first of the separate power supplies failing below a predetermined minimum power level.

9. A system according to claim 8, wherein the alarm comprises an audible alarm.

10. A system according to claim 1, wherein the remote processor is programmed to receive a unique identification for the medical treatment apparatus during a first communication with the medical treatment apparatus.

11. A system according to claim 10, wherein all subsequent communications between the medical treatment apparatus and the remote control device include the unique identification for the medical treatment apparatus.

12. A system according to claim 1, wherein the remote processor is programmed to send a unique identification for the remote control device during a first communication with the medical treatment apparatus.

13. A system according to claim 12, wherein all subsequent communications between the medical treatment apparatus and the remote control device includes the unique identification for the remote control device.

14. A system according to claim 1, wherein the separate power supplies include a general purpose power supply and a dedicated power supply and the remote control device is adapted to use the dedicated power supply only for functions related to communications between the medical treatment apparatus and the remote control device.

15. A system according to claim 14, wherein the general purpose power supply comprises a battery.

16. A system according to claim 14, wherein the general purpose power supply is user-replaceable.

17. A system according to claim 14, wherein the dedicated power supply comprises a capacitor.

18. A system according to claim 14, wherein the dedicated power supply is unitarily integrated as part of the remote control device.

19. A system according to claim 14, wherein the remote processor is programmed to use the dedicated power supply upon a measured power level of the general purpose power supply falling below a predetermined minimum power level.

20. A system according to claim 1, wherein the medical treatment apparatus comprises a fluid delivery device also including:
  an exit port assembly, and
  a dispenser for causing fluid from a reservoir to flow to the exit port assembly,
  wherein the local processor is connected to the dispenser and is programmed to cause fluid flow to the exit port assembly based upon flow instructions.

21. A system according to claim 20, wherein the exit port assembly of the fluid delivery device includes a transcutaneous access tool.

22. A system according to claim 20, wherein the local processor is programmed to cause fluid flow to the exit port assembly only upon receiving the flow instructions from the remote control device.

23. A system according to claim 20, wherein the fluid delivery device is packaged in a container for shipping and handling prior to use.

24. A system according to claim 20, wherein:
  the local processor of the fluid delivery device is programmed to cause a flow of fluid to the exit port assembly based solely on flow instructions from the separate, remote control device;
  the local communication unit includes a wireless receiver for receiving the flow instructions and delivering the flow instructions to the local processor;
  the remote communication unit of the remote control device includes a remote transmitter for sending the flow instructions to the local receiver; and
  the user interface components of the remote control device include input components connected to the remote processor for allowing a user to enter the flow instructions.

25. A system according to claim 24, wherein the fluid delivery device includes a housing containing the exit port assembly, the dispenser, the local processor, and the wireless receiver, and wherein the housing is free of user input components for providing the flow instructions to the local processor.

26. A system according to claim 20, wherein:
  the local processor of the fluid delivery device is programmed to provide flow information;
  the local communication unit includes a wireless transmitter for transmitting the flow information from the local processor;
  the remote communication unit of the remote control device includes a remote receiver for receiving the flow information from the local transmitter; and
  the user interface components of the remote control device include output components connected to the remote processor for allowing a user to receive the flow information.

27. A system according to claim 26, wherein the fluid delivery device includes a housing containing the exit port assembly, the dispenser, the local processor, and the local communication unit, and wherein the housing is free of user output components for providing the flow information from the local processor to a user.

28. A system according to claim 26, wherein:
  the local processor is programmed to receive at least some of the flow instructions from the remote control unit;
  the local communication unit also includes a wireless receiver connected to the local processor;
  the remote communication unit of the remote control device includes a remote transmitter for sending the flow instructions to the local receiver; and
  the user interface components of the remote control device include input components connected to the remote processor for allowing a user to enter the flow instructions.

29. A kit including a system according to claim 20, and further comprising a subcutaneous access tool for connection to the exit port assembly of the fluid delivery device.

30. A kit according to claim 29, including one of the remote control device, a plurality of the fluid delivery devices, and a plurality of subcutaneous access tools for connection to the exit ports of the fluid delivery device.

31. A kit according to claim 30, wherein each fluid delivery device includes a bar code.

32. A system according to claim 20, wherein the fluid delivery device further comprises a reservoir, and the dispenser controls fluid flow from the reservoir to the exit port assembly.

33. A system according to claim 32, wherein the fluid delivery device further comprises a fill port connected to the reservoir.

34. A system according to claim 32, wherein the reservoir contains a therapeutic fluid.

35. A system according to claim 34, wherein the fluid comprises insulin.

36. A system for providing medical treatment to a patient, comprising:
  A) a medical treatment apparatus including,
    a local processor, and
    a local communication element connected to the local processor;
  B) a remote control device separate from the medical treatment apparatus and including,
    a remote processor,
    user interface components connected to the remote processor,
    a remote communication element connected to the remote processor and adapted to communicate with the local communication element of the medical treatment apparatus in a wireless manner such that information can be transferred between the local processor and the remote processor, and
    a power supply connected to the remote processor, wherein the remote processor is programmed to only conduct functions related to the transfer of information between the local processor and the remote processor upon a measured power level of the power supply falling below a predetermined minimum power level.

37. A system according to claim 36, wherein the power supply comprises a battery.

38. A system according to claim 36, wherein the power supply is user-replaceable.

39. A system according to claim 36, wherein the remote processor is programmed to ignore hysteresis in the measured power level.

40. A system according to claim 36, wherein the medical treatment apparatus includes a unique identification included in all communications between the medical treatment apparatus and the remote control device.

41. A system according to claim 36, wherein the remote control device includes a unique identification included in all communications between the medical treatment apparatus and the remote control device.

42. A system according to claim 36, wherein the medical treatment apparatus comprises one of an external infusion pump, an implanted infusion pump, a pacemaker, a cardiac defibrillator, a neurostimulator, an x-ray machine, an EKG machine, a diagnostic device, a glucometer, a blood analyzer, an electrocautery device, an operating room table, a monitor, and a laparoscopic controller.

43. A system according to claim 36, wherein the remote control device is also adapted to function as at least one of a cellular phone, a personal digital assistant, and an electronic game.

44. A system according to claim 36, wherein the remote control device further includes electronic memory storing a user manual for the medical treatment apparatus.

45. A system according to claim 36, wherein the wireless communication between the remote control device and the medical treatment apparatus is radio frequency signals.

46. A system according to claim 36, wherein the remote control device further includes an alarm connected to the remote processor and the remote processor is programmed to activate the alarm upon the measured power level of the power supply falling below the predetermined minimum power level.

47. A system according to claim 46, wherein the alarm comprises an audible alarm.

48. A system according to claim 36, wherein the remote processor is programmed to receive a unique identification for the medical treatment apparatus during a first communication with the medical treatment apparatus.

49. A system according to claim 48, wherein all subsequent communications between the medical treatment apparatus and the remote control device include the unique identification for the medical treatment apparatus.

50. A system according to claim 36, wherein the remote processor is programmed to send a unique identification for the remote control device during a first communication with the medical treatment apparatus.

51. A system according to claim 50, wherein all subsequent communications between the medical treatment apparatus and the remote control device includes the unique identification for the remote control device.

52. A system according to claim 36, wherein the medical treatment apparatus comprises a fluid delivery device also including:
   an exit port assembly, and
   a dispenser for causing fluid from a reservoir to flow to the exit port assembly,
   wherein the local processor is connected to the dispenser and is programmed to cause fluid flow to the exit port assembly based upon flow instructions.

53. A system according to claim 52, wherein the exit port assembly of the fluid delivery device includes a transcutaneous access tool.

54. A system according to claim 52, wherein the local processor is programmed to cause fluid flow to the exit port assembly only upon receiving the flow instructions from the remote control device.

55. A system according to claim 52, wherein the fluid delivery device is packaged in a container for shipping and handling prior to use.

56. A system according to claim 52, wherein:
   the local processor of the fluid delivery device is programmed to cause a flow of fluid to the exit port assembly based solely on flow instructions from the separate, remote control device;
   the local communication unit includes a wireless receiver for receiving the flow instructions and delivering the flow instructions to the local processor;
   the remote communication unit of the remote control device includes a remote transmitter for sending the flow instructions to the local receiver; and
   the user interface components of the remote control device include input components connected to the remote processor for allowing a user to enter the flow instructions.

57. A system according to claim 56, wherein the fluid delivery device includes a housing containing the exit port assembly, the dispenser, the local processor, and the wireless receiver, and wherein the housing is free of user input components for providing the flow instructions to the local processor.

58. A system according to claim 52, wherein:
   the local processor of the fluid delivery device is programmed to provide flow information;
   the local communication unit includes a wireless transmitter for transmitting the flow information from the local processor;
   the remote communication unit of the remote control device includes a remote receiver for receiving the flow information from the local transmitter; and
   the user interface components of the remote control device include output components connected to the remote processor for allowing a user to receive the flow information.

59. A system according to claim 58, wherein the fluid delivery device includes a housing containing the exit port assembly, the dispenser, the local processor, and the local communication unit, and wherein the housing is free of user output components for providing the flow information from the local processor to a user.

60. A system according to claim 59, wherein:
   the local processor is programmed to receive at least some of the flow instructions from the remote control unit;
   the local communication unit also includes a wireless receiver connected to the local processor;
   the remote communication unit of the remote control device includes a remote transmitter for sending the flow instructions to the local receiver; and
   the user interface components of the remote control device include input components connected to the remote processor for allowing a user to enter the flow instructions.

61. A kit including a system according to claim 52, and further comprising a subcutaneous access tool for connection to the exit port assembly of the fluid delivery device.

62. A kit according to claim 61, including one of the remote control device, a plurality of the fluid delivery devices, and a plurality of subcutaneous access tools for connection to the exit ports of the fluid delivery device.

63. A kit according to claim 62, wherein each fluid delivery device includes a bar code.

64. A system according to claim 52, wherein the fluid delivery device further comprises a reservoir, and the dispenser controls fluid flow from the reservoir to the exit port assembly.

65. A system according to claim 64, wherein the fluid delivery device further comprises a fill port connected to the reservoir.

66. A system according to claim 64, wherein the reservoir contains a therapeutic fluid.

67. A system according to claim 66, wherein the fluid comprises insulin.

* * * * *